(12) United States Patent
Clinton et al.

(10) Patent No.: US 10,837,913 B2
(45) Date of Patent: **\*Nov. 17, 2020**

(54) DETECTION MODULE FOR AN APPARATUS FOR CONDUCTING LUMINESCENCE ASSAYS COMPRISING A REPLACEABLE DETECTION MODULE

(71) Applicant: MESO SCALE TECHNOLOGIES, LLC, Rockville, MD (US)

(72) Inventors: Charles M. Clinton, Clarksburg, MD (US); Jacob N. Wohlstadter, Potomac, MD (US)

(73) Assignee: MESO SCALE TECHNOLOGIES, LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/455,392

(22) Filed: Jun. 27, 2019

(65) Prior Publication Data

US 2020/0001288 A1    Jan. 2, 2020

Related U.S. Application Data

(63) Continuation of application No. 15/138,186, filed on Apr. 25, 2016, now Pat. No. 10,337,999, which is a continuation of application No. 12/932,836, filed on Mar. 8, 2011, now Pat. No. 9,322,783.

(60) Provisional application No. 61/339,790, filed on Mar. 9, 2010, provisional application No. 61/339,789, filed on Mar. 9, 2010.

(51) Int. Cl.
*B01L 3/00* (2006.01)
*G01N 21/76* (2006.01)
*G01N 21/64* (2006.01)
*G01N 33/543* (2006.01)

(52) U.S. Cl.
CPC ............. *G01N 21/76* (2013.01); *B01L 3/502* (2013.01); *G01N 21/6452* (2013.01); *G01N 33/54366* (2013.01); *B01L 2200/025* (2013.01); *B01L 2200/18* (2013.01); *B01L 2300/021* (2013.01); *B01L 2300/0609* (2013.01); *B01L 2300/0654* (2013.01); *B01L 2300/0663* (2013.01); *B01L 2300/0829* (2013.01); *B01L 2300/0867* (2013.01); *G01N 2201/068* (2013.01); *G01N 2201/12* (2013.01)

(58) Field of Classification Search
CPC ..... B01L 2300/0609; B01L 2300/0829; B01L 3/502; B01L 2200/027; B01L 2200/16; B01L 2300/0636; B01L 2400/0487; B01L 3/502715; B01L 9/527; G01N 21/76; G01N 21/6452; G01N 35/1011
USPC .............................. 250/221, 239, 573, 559.4
See application file for complete search history.

(56) References Cited

U.S. PATENT DOCUMENTS

| | | | |
|---|---|---|---|
| 5,104,621 | A | 4/1992 | Pfost |
| 7,842,246 | B2 | 11/2010 | Wohlstadter et al. |
| 9,784,685 | B2 * | 10/2017 | Atzler .................. G01N 35/028 |
| 2004/0022677 | A1 | 2/2004 | Wohlstadter et al. |
| 2005/0052646 | A1 | 3/2005 | Wohlstadter et al. |
| 2005/0142033 | A1 | 6/2005 | Glezer et al. |
| 2007/0231217 | A1 | 10/2007 | Clinton et al. |

(Continued)

*Primary Examiner* — Que Tan Le
(74) *Attorney, Agent, or Firm* — Nixon & Vanderhye, P.C.

(57) ABSTRACT

We describe a detection module useful with an apparatus and/or system for conducting luminescence assays, and a kit, a system, an apparatus, and a method incorporating the detection module.

28 Claims, 6 Drawing Sheets

(56) References Cited

U.S. PATENT DOCUMENTS

| | | |
|---|---|---|
| 2009/0263904 A1 | 10/2009 | Clinton et al. |
| 2011/0020178 A1 | 1/2011 | Clinton et al. |
| 2011/0022331 A1 | 1/2011 | Clinton et al. |
| 2011/0059870 A1 | 3/2011 | Wohlstadter et al. |
| 2011/0143947 A1 | 6/2011 | Chamberlin et al. |
| 2011/0203924 A1 | 8/2011 | Wohlstadter et al. |
| 2011/0256630 A1 | 8/2011 | Clinton et al. |
| 2011/0269642 A1 | 11/2011 | Glezer et al. |
| 2012/0190590 A1 | 7/2012 | Wohlstadter et al. |
| 2012/0190591 A1 | 7/2012 | Wohlstadter et al. |
| 2012/0195800 A1 | 8/2012 | Clinton et al. |
| 2013/0203620 A1 | 8/2013 | Glezer et al. |

\* cited by examiner

DETECTION MODULE FOR AN APPARATUS FOR CONDUCTING LUMINESCENCE ASSAYS COMPRISING A REPLACEABLE DETECTION MODULE

CROSS REFERENCE TO RELATED APPLICATIONS

This application is a continuation of U.S. application Ser. No. 15/138,186 filed Apr. 25, 2016, now U.S. Pat. No. 10,337,999 dated Jul. 2, 2019 which is a continuation of U.S. application Ser. No. 12/932,836, filed Mar. 8, 2011, now U.S. Pat. No. 9,322,783 issued Apr. 26, 2016; which claims the benefit of U.S. Provisional Application Nos. 61/339,790 and 61/339,789, each filed on Mar. 9, 2010, each disclosure of which is incorporated herein by reference in its entirety; this application is related to U.S. Provisional Application No. 61/123,975, filed Apr. 11, 2008; U.S. Provisional Application No. 60/752,475, filed Dec. 21, 2005; U.S. Provisional Application No. 60/726,023, filed Oct. 11, 2005; U.S. Provisional Application No. 60/752,513, filed Dec. 21, 2005; U.S. application Ser. No. 11/642,970, filed Dec. 21, 2006; U.S. application Ser. No. 11/642,968, filed Dec. 21, 2006; and U.S. application Ser. No. 12/422,081, filed Apr. 10, 2009, the disclosures of each of these applications are incorporated herein by reference in their entireties.

FIELD OF THE INVENTION

The invention relates to a detection module used in an apparatus and/or system for conducting assays. Certain embodiments of the apparatus and/or system may be used for conducting automated sampling, sample preparation, and/or sample analysis in a multi-well plate assay format.

BACKGROUND OF THE INVENTION

Numerous methods and systems have been developed for conducting chemical, biochemical, and/or biological assays. These methods and systems are essential in a variety of applications including medical diagnostics, food and beverage testing, environmental monitoring, manufacturing quality control, drug discovery, and basic scientific research.

A variety of plate readers are available for conducting assay measurements in multi-well plates including readers that measure changes in optical absorbance, emission of luminescence (e.g., fluorescence, phosphorescence, chemiluminescence, and electrochemiluminescence), emission of radiation, changes in light scattering, and changes in a magnetic field. U.S. Patent Application Publications 2004/0022677 and 2005/0052646 of U.S. patent application Ser. Nos. 10/185,274 and 10/185,363, respectively, of Wohlstadter et al. describe solutions that are useful for carrying out singleplex and multiplex ECL assays in a multi-well plate format. They include plates that comprise a plate top with through-holes that form the walls of the wells and a plate bottom that is sealed against the plate top to form the bottom of the wells. The plate bottom has patterned conductive layers that provide the wells with electrode surfaces that act as both solid phase supports for binding reactions as well as electrodes for inducing electrochemiluminescence (ECL). The conductive layers may also include electrical contacts for applying electrical energy to the electrode surfaces.

Prior plate readers, including those capable of forming an image of luminescence generated in the plate wells, contain a detection mechanism that is an inseparable, integrated part of the plate reading apparatus. Repair of a component of the detection mechanism is, therefore, carried out in a piecemeal manner. In addition, a design or engineering change to one or more components of the apparatus that could function independently of the detection mechanism, such as a plate stacker, might require a consequent re-design of detection mechanism components physically associated with or otherwise impacted by such a changed apparatus component. Such alterations might lead to inconsistent performance within or across product lines despite their using the same basic detection components. Yet, detection systems serve a core function to all luminescence based readers, in contrast to those mechanisms that serve to receive the samples and deliver them into the system in any one of a number of formats (e.g., plates, cartridges, flow cells). Therefore, there is a need for a core detection module that can be manufactured, serviced, replaced, and integrated interchangeably into a variety of reading apparatuses as a self-contained sub-assembly.

SUMMARY OF THE INVENTION

The invention provides a detection module for use with an apparatus for conducting luminescence assays, the apparatus comprising one or more detection module engagement elements, the detection module comprising a housing with the following components disposed within the housing: (a) a light detector; and (b) a control board comprising (i) a microcontroller; (ii) motion control and communications electronics; (iii) an external input/output connector; and (iv) an internal input/output connector, wherein the housing comprises one or more apparatus engagement elements configured to align and engage with the one or more detection module engagement elements. In a preferred embodiment, the apparatus is configured to conduct a luminescence assay using a multi-well assay plate.

Also provided is a system comprising (a) an apparatus for conducting luminescence assays in multi-well plates, the apparatus comprising a light-tight enclosure (LTE), a fluidic assembly, an imaging assembly, a plate assembly capable of supporting and translating a plate to one or more components of said apparatus; and one or more detection module engagement elements; (b) a detection module for use with the apparatus, the detection module comprising a housing with the following components disposed within the housing: (x) a light detector; and (y) a control board comprising (i) a microcontroller; (ii) motion control and communications electronics; (iii) an external input/output connector; and (iv) an internal input/output connector, wherein the housing comprises one or more apparatus engagement elements configured to align and engage with the one or more detection module engagement elements.

Still further, the invention contemplates a method of conducting a luminescence assay in an assay system as described herein comprising: (a) inserting the detection module into the apparatus; (b) engaging the apparatus and detection module engagement elements; (c) inserting the multi-well assay plate within a light-tight enclosure of the apparatus; (d) generating a current/voltage waveform in the detection module; (e) providing electrical energy to a well of the assay plate in the light-tight enclosure; and (f) measuring luminescence from the assay plate in the detection module.

The invention also provides an apparatus for conducting luminescence assays in multi-well plates, the apparatus comprising a light-tight enclosure (LTE), a fluidic assembly, an imaging assembly, a plate assembly capable of supporting and translating a plate to one or more components of the apparatus; and one or more detection module engagement elements configured to align and engage with a detection module via one or more apparatus engagement elements position on the detection module.

The invention further provides a kit comprising a detection module as described herein and a device comprising software to (i) operate said detection module and/or said apparatus, and/or (ii) manage and/or analyze data collected on said apparatus and/or detection module.

DESCRIPTION OF SPECIFIC EMBODIMENTS OF THE INVENTION

Figure 1A:
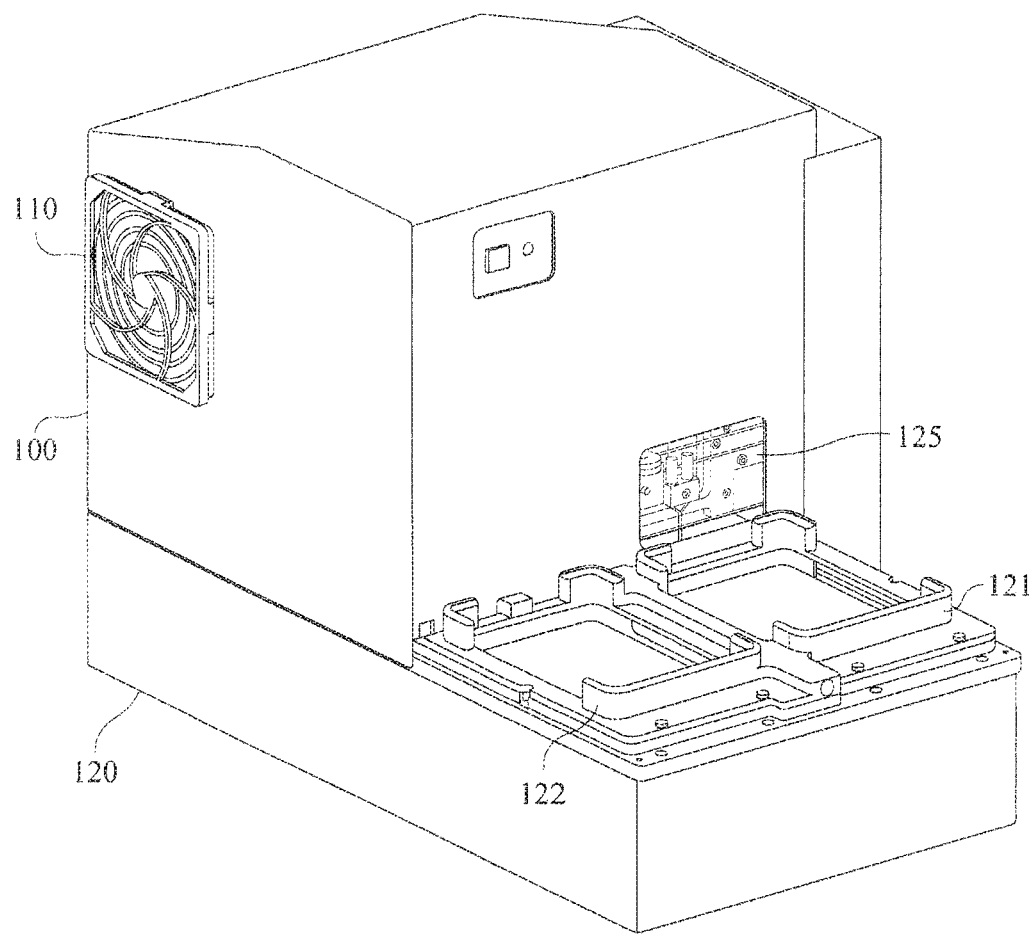
FIG. 1A shows a view of one embodiment of an assay system of the invention, including a detection module aligned and engaged with an apparatus.

The Detailed Description section provides descriptions of certain embodiments of the invention that should not be considered limiting but are intended to illustrate certain inventive aspects. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

Described herein is a detection module used with an apparatus for conducting luminescence assays. As used herein, an assay system refers to the apparatus including an integrated detection module, i.e., a detection module that is mounted to and properly aligned with an apparatus. The detection module is a single, self-contained, replaceable unit within a housing comprising various components used with an apparatus, e.g., a camera and lens, a main control printed circuit board including an optional computer module, and associated mechanical structural components and cabling. The components within the detection module interface with the apparatus upon proper alignment and engagement of the detection module to enable the conduct of an assay with the apparatus/assay system. A detection module of the present invention provides standardized manufacturing and performance characteristics across a range of apparatus formats into which it may be integrated.

The detection module includes one or more alignment and engagement elements that mate to one or more apparatus alignment and engagement elements, to support and ensure the proper alignment of the detection module within the apparatus. These elements can include engagement elements such as tabs, slots, pins, guide holes, latches, locking mechanisms, and the like. In the detection module, the one or more alignment and engagement elements are referred to as "apparatus engagement elements" because they facilitate proper alignment and engagement of the detection module with the apparatus. Likewise, the one or more alignment and engagement elements of the apparatus are referred to as "detection module engagement elements." In one embodiment, the detection module comprises a vertical tab and the apparatus comprises an engagement pin. When the detection module is inserted into the apparatus, the vertical tab of the detection module contacts the engagement pin, causing the detection module to lock into proper orientation within the apparatus. The apparatus may also include a guide surface adapted to receive and guide the detection module into position within the apparatus. Alternatively, the apparatus may include a locking mechanism comprising a spring loaded latch and a first pin configured to engage with the detection module and a second pin configured to engage with a notch on the detection module, wherein movement of the detection module into the apparatus contacts the first pin causing the latch to rotate and the second pin to engage with the notch. The spring loaded rotating latch may include a spring to resist the rotation of the latch, and optionally, the resistance of the spring is reduced as the second pin engages with the notch. The latch may also include a tab and the locking mechanism further comprises an optical sensor, wherein the tab is configured to cover the optical sensor when the locking mechanism is engaged. The tab may include a pin extending down toward the optical sensor.

FIG. 1A shows a view of one embodiment of an assay system of the invention surrounded by system housing 100. FIG. 1A shows the relative position of the light-tight enclosure 120, input and output plate stackers, 121 and 122, respectively, which are adapted to hold multi-well assay plates for use in assays conducted in the system, and window 125, which provides an optical path for a bar code reader (not shown) in the fluidic subsystem within the apparatus (not shown) to read bar codes on plates in input stacker 121.

Figure 1B:
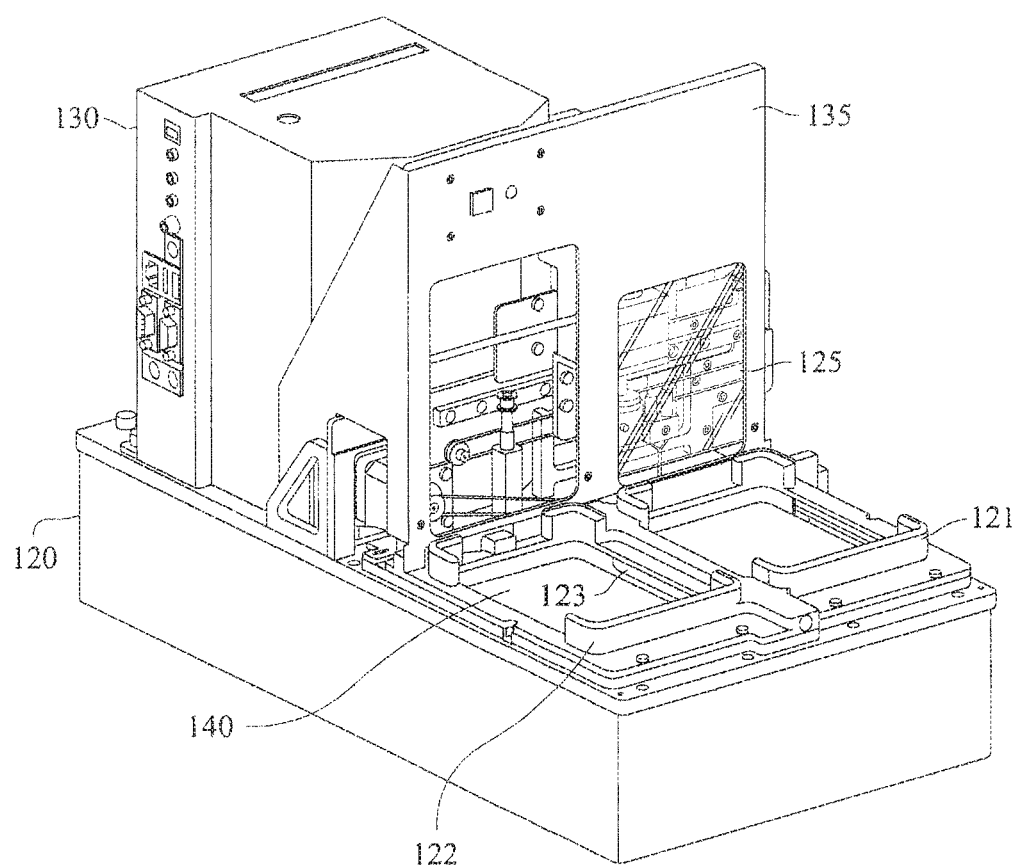
FIGS. 1B-1C provide an isometric view of one embodiment of the assay system and a corresponding side view, respectively.
Figure 1C:
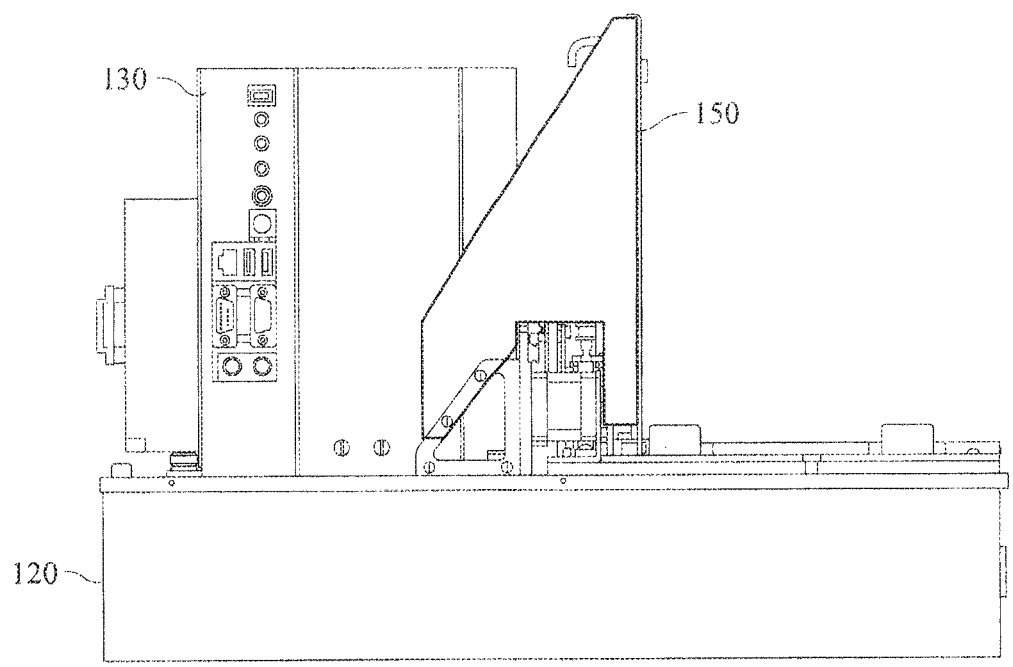

FIG. 1B provides an isometric view of one embodiment of the assay system with system housing 100 removed and incorporating detection module 130, aligned and engaged with apparatus 110 (which includes elements 120, 121, 122, 123, 125, 135, and 140). Sliding light-tight door 140 provides a light-tight seal to plate introduction apertures (not shown) in the top of light-tight enclosure 120 located under plate stackers 121 and 122. Plate stackers 121 and 122 have plate release latches 123 that are spring loaded to allow plates raised from the light-tight enclosure below (using a plate elevator that is not shown in this view) to be captured in the stack. The latches in the input stack can also be directed to be released to allow plates to be released from the stack to a plate elevator below (not shown). A side view of the apparatus is shown in FIG. 1C, in which detection module, 130, is aligned with apparatus 110 and positioned on top of light-tight enclosure of the apparatus, 120, adjacent to a fluidic subsystem of the apparatus (not shown in this view), which is surrounded by support bracket 150 (also a component of the apparatus).

Figure 2:
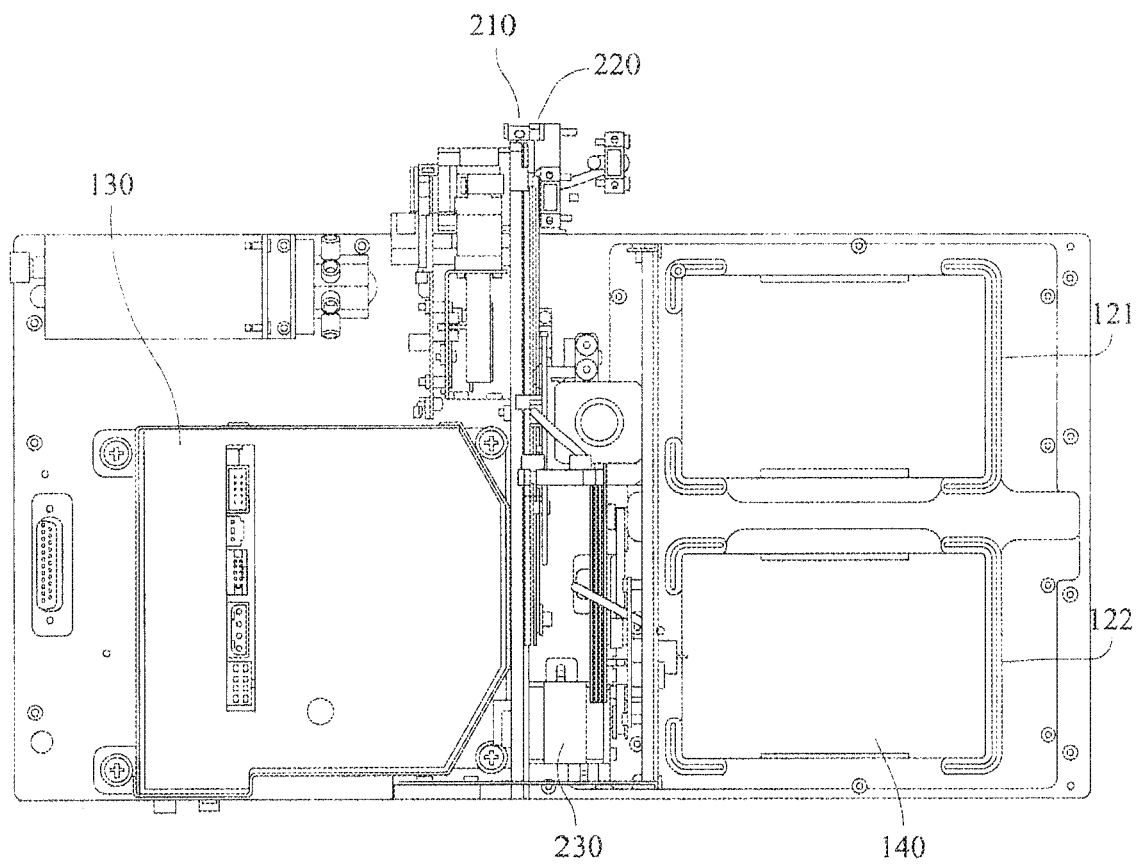
FIG. 2 shows a top view of an assay system of the invention.

FIG. 2 shows a top view of the apparatus, including detection module 130 aligned with the apparatus, including input and output plate stackers, 121 and 122, and plate translation stage, 210. Fluidic subsystem (220) is used to deliver sample to the apparatus, wash the integrated pipettor (not shown), and dispose of waste from the pipettor (not shown). Motor 230 is coupled via a belt to a linear screw drive (not shown) that opens door 140. Pipetting probe translation stage 160 provides horizontal and vertical translation of dual pipetting probe (not shown) and a piercing tool (not shown) is used to pierce and displace seals on wells of sealed plates so as to allow for unblocked imaging of the wells.

Figure 3A:
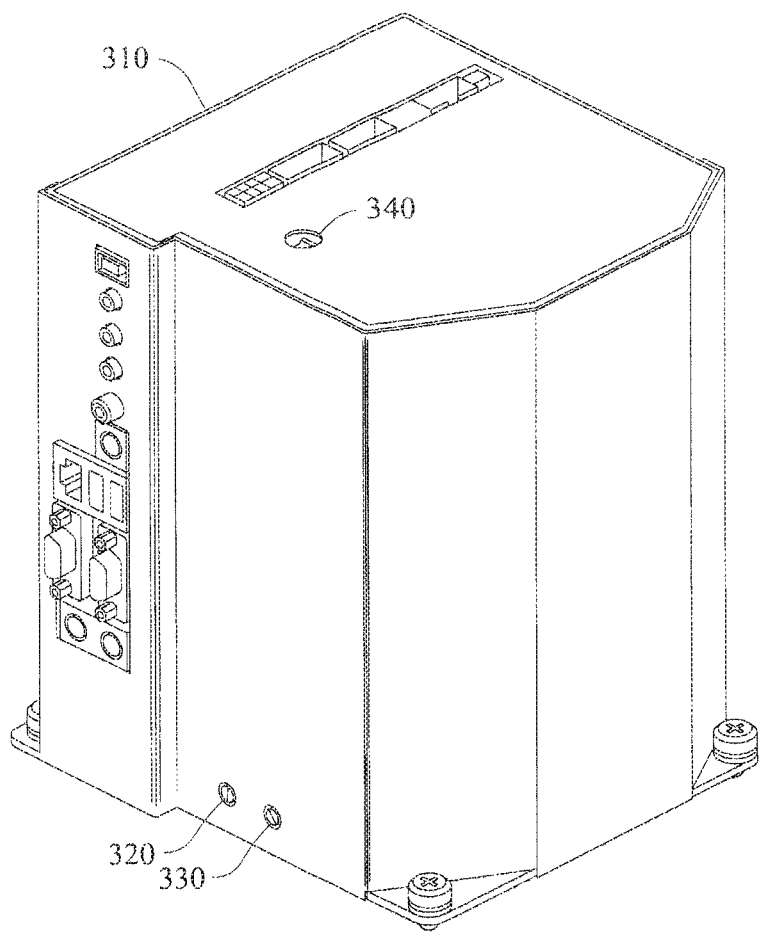
FIGS. 3A-3B is a view of the detection module of the invention with the housing (FIG. 3A) and the various components of imaging system within the housing (FIG. 3B).

The module may include alignment mechanisms for adjusting the alignment of internal module components after the module has been attached to an apparatus. FIG. 3A is a view of the detection module with a detection module housing (310), including alignment mechanisms for X, Y, and Z-adjustment (320, 330 and 340, respectively) of the camera and lens within the detection module. In the specific embodiment shown in the figure, set screws are used to align in the X and Y directions and a drive screw is used to focus the optical system in the Z direction. A wide range of alternative alignment mechanisms will be known to one of average skill in the art. The alignment mechanisms can be configured to be adjusted manually or, alternatively, can be motorized to enable automated alignment.

Figure 3B:
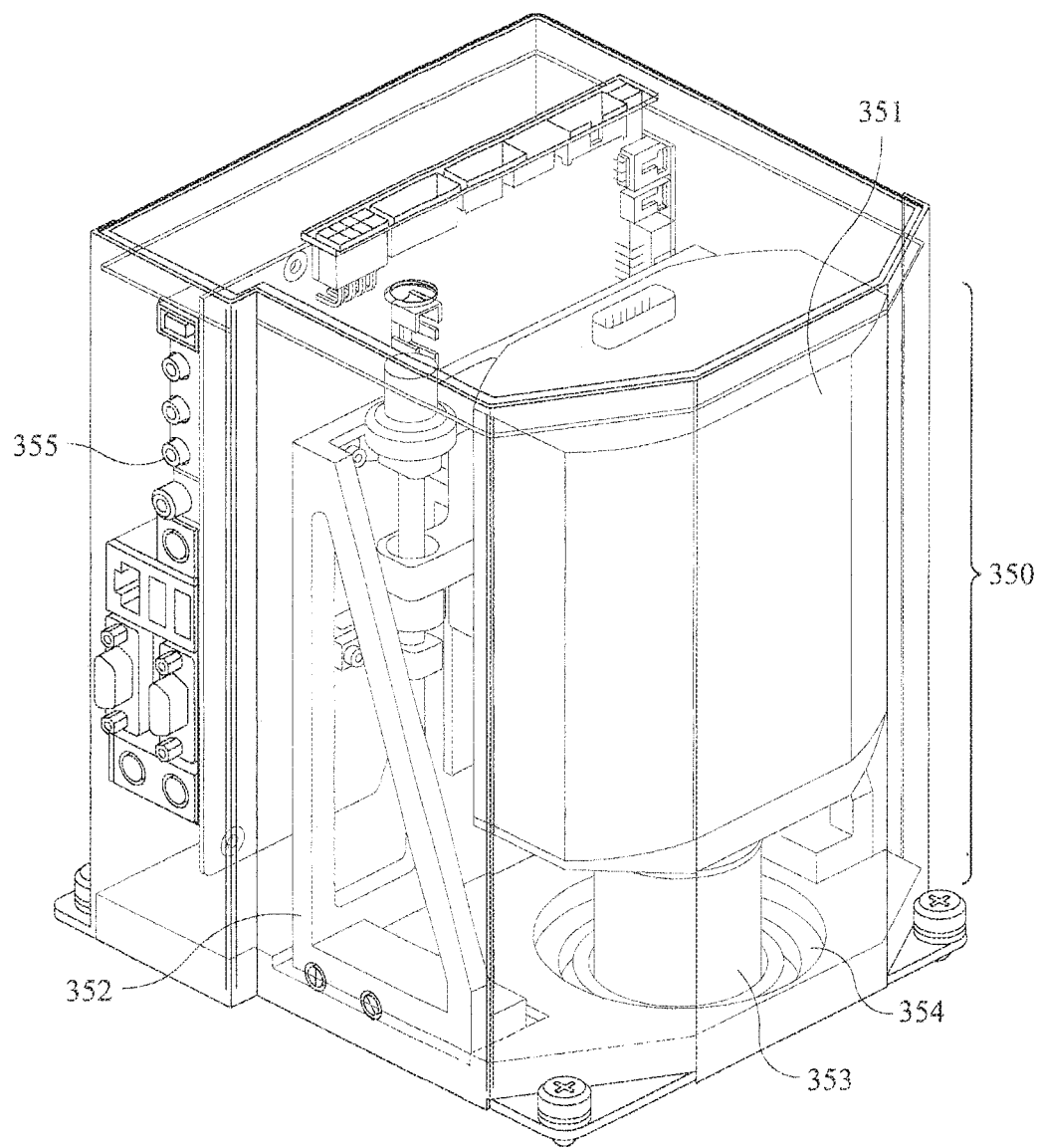

FIG. 3B shows the various components of imaging system 350 within the housing of the detection module. The imaging system includes a camera 351 mounted on the top of light-tight enclosure (not shown) via camera bracket 352. Lens 353, coupled to camera 351, is used to provide a focused image of luminescence generated from plates in the light-tight enclosure. Diaphragm 354 sealed to lens 353 and an aperture in the top of the light-tight enclosure, allows imaging system 350 to image light from the light-tight enclosure while maintaining the enclosure in a light-tight environment protected from environmental light. The main control board 355 is also positioned within the detection module and includes a microcontroller, motion control and communication electronics, a computer module, external and internal input/output connectors (not specifically shown).

In one embodiment, the invention provides a detection module comprising a housing with the following components disposed within the housing: (a) a light detector; and (b) a control board comprising (i) a microcontroller; (ii) motion control and communications electronics; (iii) optionally, a computer module; (iv) an external input/output connector; and (v) an internal input/output connector. As discussed above, the detection module housing element is configured for placement within the apparatus. Providing a single, self-contained, replaceable detection module that may be used with an apparatus in an assay system provides a number of significant benefits, including but not limited to, efficiencies in the manufacturing process and simplified maintenance and service of the assay system and its component parts. Moreover, as discussed in more detail below, because various different detection modules may be used with a single apparatus, the present invention provides enhanced flexibility to the user that requires a range of results that may not be achieved with a single fully integrated system.

The detection module is configured to interface with the various components of the apparatus to control the mechanical and/or electronic subsystems of the apparatus, analyzing the acquired data and/or delivering analyzed data to a component of the apparatus, e.g., a user and/or system interface. In one embodiment, the microcontroller of the detection module comprises firmware that interfaces with the software running on the apparatus. The firmware provides an interface that supports one or more of the following detection module functions: analog input, digital input, digital output, PCB interrupt status, stepper motor control, and ECL waveform generation and electrode impedance measurements. In addition, the firmware enables board identification, operating status, and firmware revision management within the detection module.

The detection module light detector may be a conventional light detector such as a photodiode, avalanche photodiode, photomultiplier tube, or the like. Suitable light detectors also include arrays of a plurality of light detectors. Light detectors that may be used also include imaging systems such as CCD and CMOS cameras. The light detector also includes optics which collect light emitted from a multi-well assay plate and focus that light on the light detector. Optics may also include, e.g., elements that transmit, scatter, block, filter, modify, diffract, refract, and/or reflect light. Optics may include physical/mechanical elements that provide structural support or couple the optical elements to other elements of the apparatus. Examples of optics include but are not limited to lenses, prisms, filters, splitters, mirrors, optical fibers, optical couplers, optical epoxies and adhesives, windows, modulators, optical coatings and the like. The lens may be a high numerical aperture lens which may be made from glass or injection-molded plastic. CCD or CMOS cameras used in the module may be uncooled or may be cooled to, e.g., 0° C., −10° C., −20° C., −40° C. or lower depending on sensitivity requirements. In addition, optics may include filters designed to selectively pass the luminescence generated from transition metal labels, particularly ruthenium-tris-bipyridine labels. In a specific embodiment, the optics include a lens and a filter for directing, focusing and/or imaging light on the detector. The light detector may also incorporate control electronics, software, firmware, connectors, and high speed cables for efficient transfer of images to the electronics and computer within the apparatus and/or the detection module.

In one specific embodiment, the light detector comprises a lens, an optical filter and a photodetector, e.g., a CCD camera. In one embodiment, the light detector comprises a CCD camera comprising firmware. In addition, the light detector may include a diaphragm sealed to the lens and a detection module aperture in vertical alignment with a light-tight enclosure aperture to allow the light detector to image light from the light-tight enclosure while maintaining the light-tight enclosure in a light-tight environment protected from ambient light. In one specific embodiment, the components of the light detector, e.g., the photodetector comprising an imaging element, coupled to a lens, a filter element and a diaphragm, are positioned above the detection module aperture and in vertical alignment with the light-tight enclosure aperture. In certain embodiments, an imaging element is used to image luminescence from arrays of binding domains in one or more wells of an assay plate and/or one or more regions of an assay cartridge positioned within the apparatus and the assay apparatus reports luminescence values for luminescence emitted from individual elements of the arrays.

Optionally, the detection module may further include a mechanism, e.g., a wheel, ring or a through-hole into which a tool may be inserted for adjustment, located on the outside of the detection module housing, that may be used to manually control the movement of the light detector along a vertical axis within the housing to control the focusing of the light detector within the detection module. In one embodiment, the detection module may attach to a mount in the apparatus that comprises a manual or automated axis of motion for moving the detection module up and down. Optionally, the detection module may remain static once placed within the apparatus, but the light detector components may move within the detection module, controlled by an axis external to the module housing. Still further, the light detector components may move independently from the PCB located within the detection module. Alternatively, focus may be controlled by one or more printed circuit boards and associated firmware within the detection module housing.

In a specific embodiment, the imaging system within the detection module is capable of automatic X, Y and/or Z-training on an object within the light-tight enclosure once the detection module is positioned within the chassis of the apparatus. For example, in order to insure proper alignment of the optical components within the apparatus, the imaging system is programmed to focus on a pre-defined component or target positioned within the light-tight enclosure, e.g., on the plate carriage, a test plate, cartridge, etc. and image that target to adjust and confirm proper alignment of the imaging system to the light-tight enclosure. The firmware is programmed to align the detection module, the imaging system and/or one or more components within the light-tight enclosure in response to the output of the X, Y, and/or Z-training test to confirm proper alignment of the detection module and light-tight enclosure.

An assay system and apparatus may accommodate more than one type of detection module and the components within a detection module may differ from those of another depending on the type of measurement required. One or more of the components of the detection module may vary, e.g., the type or sensitivity of the light detector, dynamic range of the camera, and/or one or more elements of the control board. In one embodiment, a first detection module may include a light detector that comprises a CCD camera and a second detection module may include a photodiode. Alternatively, a first detection module may include a single light detector and a second detection module may include an array of light detectors. The following elements/components/characteristics may also be varied in the construction of a detection module: lens design, light guide configuration, sensitivity, dynamic range detection limits, and/or temperature control, etc., and these detection module variations may lead to adjustments by the apparatus to conduct a measurement using a given detection module, e.g., the characteristics of the waveform applied by the apparatus. In one embodiment, a first detection module may include a high-resolution lens/CCD chip to yield a high-resolution detection module, and a second detection module may include a low-resolution lens/CCD chip to yield a low-resolution detection module. Alternatively, the detection module may include a plurality of CCD chips to increase the throughput of the detection module.

Still further, the apparatus may include a series of detection modules, i.e., two or more detection modules, e.g., high- and/or low-resolution modules, on a platform positioned above the light-tight enclosure. The two or more detection modules may be the same or different. In one embodiment, a first detection module may be a high-resolution module and the second detection module may be a low-resolution module. The use of two or more detection modules in an assay system increases the throughput of the system because it enables simultaneous imaging of a single multi-well plate. In this embodiment, the light-tight enclosure includes two or more apertures that may be vertically aligned with two or more detection module apertures. This configuration enables the simultaneous analysis of two or more wells of a multi-well plate, such that a first detection module and a corresponding light-tight enclosure aperture is positioned above a first well or grouping of wells in a multi-well plate and a second detection module and a corresponding light-tight enclosure aperture is positioned above a second well or grouping of wells in the multi-well plate. In a preferred embodiment, the first detection module is aligned with a corresponding light-tight enclosure aperture which is positioned above a first half of a multi-well plate and a second detection module is aligned with a corresponding light-tight enclosure aperture which is positioned above a second half of the multi-well plate.

During a measurement, a multi-well assay plate is placed within the light-tight enclosure and positioned underneath the light-tight enclosure aperture and in vertical alignment with the detection module aperture. The light detector collects an image of a well or group of wells of the multi-well plate and focuses that image onto the imaging element of the light detector. The light detector acquires and, preferably, stores a background image to the control board and sends data to a computer within or attached to the apparatus via one or more internal and/or external I/O connectors. The apparatus makes electrical contact with a well or group of wells of the plate and the light detector begins to acquire an image and the current/voltage source within the apparatus generates a waveform that is applied to the plate. The waveform may be adjusted by the apparatus depending upon the type of detection module installed in the assay system. After completion of the waveform and image, the data are transferred from the light detector and control board to a computer where they are processed. One or more assay processing steps may be modified or varied depending on the detection module installed in the assay system.

The detection module comprises an identifier and the assay system, apparatus, or a component thereof comprises an identifier controller that interacts with the identifier. As described hereinbelow, the identifier includes information concerning the detection module, which may include but is not limited to, the identity of the detection module and it's component parts (e.g., by serial and/or lot number), the configuration of the detection module, how the detection module is manufactured and handled prior to use and/or how the detection module is used in an apparatus. In one embodiment, the invention provides an apparatus configured to use a detection module in the conduct of an assay, wherein the detection module includes a detection module identifier as described herein and the apparatus includes (a) a storage medium comprising detection module data; and (b) a reader adapted to read information from the detection module identifier and relate/cross-check detection module information stored to the detection module identifier to that stored to the apparatus' storage medium. The detection module data stored to the storage medium includes detection module identification and/or configuration information and one or more steps of an assay protocol that may be applied by the apparatus in the conduct of an assay using various detection modules. Therefore, the detection module identifier includes information that may be used to identify a specific detection module, e.g., a serial number for an individual detection module, and the corresponding detection module data stored to the apparatus includes information that is used to identify a detection module associated with the apparatus as well as information that is used by the apparatus once the detection module is identified to carry out an assay protocol using that detection module. Alternatively, the detection module information stored to the identifier includes all the information required to identify and appropriately configure/adjust the apparatus for use of the detection module.

In one embodiment, one or more steps of an assay protocol may be tailored to an individual detection module. One or more steps of a protocol may differ from individual detection module to detection module and the detection module data and/or information stored to the apparatus and detection module identifier, respectively, includes instructions to tailor those steps of the assay protocol for a given detection module. This type of detection module data and/or information may be used by the assay system and/or apparatus to adjust one or more operations performed by the assay system and/or apparatus before, during and/or after the conduct of an assay by the assay system and/or apparatus. Moreover, this type of detection module data and/or information may optionally be adjusted by the system and/or apparatus user at the user's discretion.

In another embodiment, the detection module data and/or information further includes one or more analytical tools that may be applied by the assay system and/or apparatus to analyze data generated during and/or after the conduct of an assay. In this embodiment, the detection module data and/or information is used by the assay system and/or apparatus to adjust the analytical processing tools applied by the system and/or apparatus software in the conduct of an assay or after the assay is completed and the results are generated and/or displayed. Such analytical processing tools include but are not limited to assay thresholds and/or calibration curves that may be applied to one or more steps of an assay protocol that may also be altered based on detection module differences.

In a preferred embodiment, the detection module data and/or information may be used by the assay system and/or apparatus to adjust the operation of a component of the apparatus selected from the group consisting of one or more sensors; mechanisms to align and orient the detection module with said one or more sensors and/or with electrical, mechanical or fluidic interfaces in said apparatus, and/or to align and orient one or more assay consumables used by the apparatus in relation to the detection module and/or a component thereof. In a particularly preferred embodiment, the system and/or apparatus uses a multi-well plate or assay cartridge and the light detector within the detection module should be properly aligned and oriented with respect to a well, grouping of wells, or segment of the plate or cartridge for effective light detection during the conduct of an assay. Appropriate alignment and orientation of the light detector within the detection module may be adjusted by detection module information stored to the detection module identifier that is read and processed by the apparatus when the detection module is mated to the chassis of the apparatus. Alternatively, if the detection module is adapted to use a specific type of multi-well assay plate, it is programmed with that identification information which is used by the detection module to adjust the imaging system for analysis and image processing of that specific type of multi-well assay plate. Additionally, if a high resolution detection module is placed in an apparatus, the high resolution detection module is programmed with information to identify the specific model of detection module and the apparatus uses this identification information to adjust one or more calibration and/or assay parameters to adapt the apparatus for use with a high-resolution detection module.

In one embodiment, the detection module identifier comprises memory for storing information related to the module and its use. In one embodiment, the memory is non-volatile memory. Non-volatile memory is computer memory that can retain the stored information without power. Examples of non-volatile memory which may be used in the consumable identifier include, but are not limited to, electronic non-volatile memory (e.g., read-only memory and flash memory), magnetic memory (e.g., hard disks, floppy disk drives, and magnetic tape), optical memory (optical disc drives) and hybrids of these approaches (e.g., magneto-optical memory).

In one embodiment, the detection module identifier comprises EPROM (erasable programmable read-only memory), a type of programmable read-only memory that can be erased by exposing it to ultraviolet light. Once erased, it can be reprogrammed with new or modified data. In another embodiment, the detection module identifier comprises EEPROM (electronically erasable programmable read-only memory) a class of non-volatile electronic memory that can be electrically erased and reprogrammed without exposure to UV light. An EEPROM can be written to or programmed more than once and can be selectively programmed (the user can alter the value of certain cells without erasing the programming of the other cells). Therefore, sections of data can be erased and replaced without needing to alter or reinstall the rest of the chip's programming.

In another embodiment, the detection module identifier comprises flash memory, a specific type of EEPROM that is erased and programmed in large blocks. Although flash memory is technically a type of EEPROM, the term "EEPROM" is generally used to refer specifically to non-flash EEPROM which is erasable in small blocks, typically bytes. Because erase cycles are slow, the large block sizes used in flash memory erasing give it a significant speed advantage over conventional EEPROM when writing large amounts of data.

In another embodiment, the detection module identifier comprises a smart card, chip card, or integrated circuit card (ICC) (referred to collectively as "ICCs"). These are small cards with embedded integrated circuits which can process and store data. There are two broad categories of ICCs; i) "memory cards" that contain non-volatile memory storage components and, optionally, some specific security logic but do not contain microprocessors and i) "microprocessor cards" that combine non-volatile memory components with microprocessor components and enable the processing of information being read into or out of the ICC. The ICC electronic components are supported on a card that is, typically, made of plastic such as PVC or ABS. The card may include an embedded hologram to avoid counterfeiting. Contact ICCs have conductive contact pads. When inserted into a reader, the contact pads on the ICC make contact with electrical connectors in the reader to allow for transfer of information between the reader and the ICC, for example, allowing the reader to read, erase or write information on the ICC.

Another method of transferring information is via an RFID, i.e., radio frequency identification, which is similar in theory to bar code identification. With RFID, the electromagnetic or electrostatic coupling in the RF portion of the electromagnetic spectrum is used to transmit signals. An RFID system consists of an antenna and a transceiver, which read the radio frequency and transfers the information to a processing device, and a transponder, or tag, which is an integrated circuit containing the RF circuitry and information to be transmitted.

Identification can also be accomplished by reading a bar code. One of the key differences between RFID and bar code technology is that RFID eliminates the need for line-of-sight reading that bar coding depends on. Also, RFID scanning can be done at greater distances than bar code scanning. High frequency RFID systems (850 MHz to 950 MHz and 2.4 GHz to 2.5 GHz) offer transmission ranges of more than 90 feet, although wavelengths in the 2.4 GHz range are absorbed by water (the human body) and therefore has limitations.

In one embodiment, the non-volatile memory used in the present invention is selected from the group consisting of an EEPROM, flash memory, ICC and combinations thereof. In one embodiment, the non-volatile memory is an EEPROM. In an alternate embodiment, the non-volatile memory is an RFID.

The apparatus of the present invention includes an identifier controller that controls the operation of the non-volatile memory and other components of the apparatus. The identifier controller optionally includes a micro-controller to interface with the non-volatile memory over a communication interface, which may incorporate conventional interface architectures and protocols such as I2C, a two line serial bus protocol. The microcontroller addresses the non-volatile memory and performs write, read and erase operations on the memory.

While certain embodiments of the detection module and apparatus described herein call for the use of multi-well assay plates, this is merely for illustrative purposes and the detection module of the present invention may be integrated into any number of different assay systems and/or apparatuses to suit a given user's needs. For example, a detection module can be configured for use in an apparatus designed to analyze a sample delivered via any of a variety of sample delivery methods, e.g., multi-well assay plates, sample tubes, cartridges, and/or flow cells, and conduct a biological assay in any of a variety of assay formats. In this regard, reference is made to U.S. Pat. Nos. 6,066,448; 6,090,545; 6,140,045; 6,207,369; 7,824,925; 7,842,246; 6,977,722; 7,497,997; 7,807,448; and U.S. patent application Ser. Nos. 11/300,808; 11/642,968; 12/42,208; 12/7,966,921; and 12/844,440, the disclosures of which are incorporated herein by reference in their entireties. Moreover, the detection modules, apparatus, and assay systems described herein may be used with a variety of assay detection techniques including, but not limited to, techniques measuring one or more detectable signals. Certain embodiments are suitable for electrochemiluminescence measurements and, in particular, embodiments that are suitable for use with multi-well plates with integrated electrodes (and assay methods using these plates) such as those described in U.S. Publication Nos. 2004/0022677 and 2005/0052646 of U.S. application Ser. Nos. 10/185,274 and 10/185,363, respectively, of Wohlstadter et al., and U.S. application Ser. No. 11/642,970 of Glezer et al. ECL-based multiplexed testing is described in U.S. Publication Nos. 2004/0022677 and 2004/0052646 of U.S. application Ser. Nos. 10/185,274 and 10/185,363, respectively; U.S. Publication No. 2003/0207290 of U.S. application Ser. No. 10/238,960; U.S. Publication No. 2003/0113713 of U.S. application Ser. No. 10/238,391; U.S. Publication No. 2004/0189311 of U.S. application Ser. No. 10/744,726; and U.S. Publication No. 2005/0142033 of U.S. application Ser. No. 10/980,198.

In one embodiment the apparatus includes various components used in the conduct of an electrochemiluminescence (ECL) assay on a multi-well plate having integrated electrodes. For example, the apparatus (or reader) includes a light-tight enclosure (LTE), a fluidic assembly (including but not limited to, e.g., pumps/valves, a pipettor subassembly, a probe, fluidic sensors, fluidic lines leading to and/or from a reagent/waste subassembly and/or a wash subassembly, etc.) an imaging assembly, and an assembly capable of supporting and translating a plate to one or more components of the apparatus. The apparatus may further comprise various translation mechanisms to move additional components of the apparatus. Furthermore, the apparatus may comprise computers or other electronic systems for controlling the operation of the apparatus including, e.g., operating motorized mechanical systems and triggering and/or analyzing luminescence signals. Still further, the apparatus may include the necessary electronic components and/or active mechanical components for carrying out an assay measurement, e.g., one or more sources of electrical energy, ammeters, potentiometers, light detectors, temperature monitors or controllers, pumps, valves, a microprocessor for controlling the mechanical and/or electronic subsystems, analyzing the acquired data and/or providing a graphical user interface (GUI). These components may be conventional components such as components known in the art.

In one specific embodiment, the apparatus includes a fluidics subsystem which may comprise one or more of the following components: a pump/valve syringe, a probe, a sample station, tubing, a reagent subassembly, interface fittings for sample and/or waste, and combinations thereof. The apparatus may further include electronics selected from the group consisting of: power distribution printed circuit board (PCB), PCBs designed to control movement of probes in the X, Y or Z-axes, a contact board PCB, a motor driver PCB; a bar code reader, an elevator sensor PCB, a LTE PCB, cables, and combinations thereof. Still further, the apparatus may include a motion control subsystem including a component selected from the group consisting of: a LTE door, a plate load mechanism, a plate piercing mechanism assembly, a contact mechanism, a plate carriage, plate and probe motion control subassemblies (optionally independently controlling plate and/or probe motion in the X, Y or Z-axis), and combinations thereof. Moreover, the apparatus may include a structural component selected from the group consisting of: a LTE housing, a probe axis assembly, component support brackets, mounting frames and/or reinforcing members, and combinations thereof.

Components, sub-systems and sub-assemblies suitable for use in the apparatus are disclosed in U.S. Application Nos. 61/123,975; 60/752,475; 60/726,023; 60/752,513; 11/642,970; 11/642,968 (published as US 2007/0231217); and Ser. No. 12/422,081, the disclosures of which are incorporated herein by reference. In particular, reference is made to FIGS. 1 to 3 and the accompanying description, e.g., on page 5, of US 2007/0231217, and these specific disclosures are incorporated herein by reference in their entireties.

The external input/output connectors are selected from the group consisting of Ethernet, keyboard, mouse, video, USB, RS-232, PCMCIA cards, PCI boards, power, networking devices, modems, user input devices, display, data storage devices, and combinations thereof.

A computer within or connected to the apparatus participates in the operation, control, management of data and monitoring of the apparatus, the detection module and/or other peripheral devices. The software required to operate the apparatus and/or the detection module, manage and analyze data collected on the apparatus and/or detection module may be provided with the apparatus and/or detection module or as a separate component of the system.

The detection module, apparatus, and assay system may be specifically designed to reliably operate in a broad range of environmental conditions, including but not limited to, low pressure for altitude testing, exposure to high and low temperatures plus temperature shock (both operating and in storage), rain (including wind-blown and freezing rain), humidity, fungus, salt, fog for rust testing, sand and dust exposure, explosive atmosphere, leakage, acceleration, shock and transport shock (i.e., triangle/sine/square wave shocks), gunfire vibration, and random vibration. In a specific embodiment, the detection module, apparatus, and/or assay system is designed to comply with MIL-STD-810G, which specifically addresses shock and vibration stress, and MIL-STD-461, which addresses the requirements for the control of electromagnetic interference characteristics of subsystems and equipment.

Accordingly, the detection module and/or system housing may be fabricated, in whole or in part, from a substance selected from the group consisting of metal (steel and/or aluminum), plastic, magnesium alloy, and combinations thereof. In one embodiment, if the substance is non-metal it may be spray coated with a metal paint or conductive coating, e.g., nickel. In addition, the detection module, apparatus, and assay system may include one or more shock-mounted components and/or sealed I/O ports. The detection module and/or system housing may be electrically grounded and the components of the detection module, apparatus, and assay system each make electrical contact with one another and are grounded. The detection module and/or system housing may include one or more vents and those vents are optionally sized for EMI control, e.g., vents should comprise a round hole pattern and the holes in the pattern should be as small as practical, e.g., less than about 0.2 inches in diameter, and in one embodiment, approximately 0.125 inches in diameter. In a preferred embodiment, the vent holes are not slots. Still further, areas within the detection module, apparatus, and assay system for placement of connectors should be sized appropriately for the connector and EMI gaskets may be used to seal connectors. EMI shields may be placed directed onto printed circuit boards to enhance EMI shielding and ferrites (i.e., magnets that wrap around cables) may be used on cables external to the detection module, apparatus, and assay system to filter any EMI picket up by the cables.

Structural components of the detection module, apparatus, and assay system may be made from aluminum, titanium, or engineering plastics, such as glass-filled polymers, to maximize strength of the structure while minimizing mass. Printed circuit boards may be made from fiberglass stock of sufficient thickness to increase stiffness of the board (preferably greater than 0.062 inches, and more preferably between about 0.09 to 0.125 inches) and have additional mounting locations to minimize the effects of shock and/or vibration. Vibration isolators may be used at mounting locations. Moreover, vibration control may be achieved using passive technologies, e.g., passive damping using viscoelastic materials, viscous dampers (dashpots), tuned-mass dampers, dynamic absorbers, shunted piezoceramics dampers, and magnetic dampers. Printed circuit boards may have conformal coatings (i.e., a polymer layer applied to printed circuit board after manufacturing) to increase their resistance to high ambient humidity, salt, fog, and other environmental conditions. In addition, printed circuit boards may comprise relatively thick copper traces on the board, e.g., greater than 8 mils, and/or the boards do not include large cantilevered components to reduce the impact of shock and vibration within the detection module. The housing of the detection module, apparatus, and assay system may include seals for connectors or other openings. Cables may be strain-relieved and optionally include locking connectors on each end. In addition, fasteners may have locking features (nylon patch, loctite, lock washers, SEMS, etc.) and the lens aperture of the detector module may include a lens cover.

In one embodiment, the detection module, apparatus, and assay system may include heaters and/or coolers (e.g., a thermoelectric heater/cooler, liquid cooled pipes) and/or a desiccant chamber to maintain the detection module, apparatus, and assay system under controlled temperature and/or humidity. In addition, the detection module, apparatus, and assay system may include a ventilation mechanism, e.g., a fan, to control temperature within the detection module, apparatus, and assay system.

Patents, patent applications, publications, and test methods cited in this disclosure are incorporated herein by reference in their entirety.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the claims.

A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

We claim:

1. A detection module configured for placement and functional engagement with an apparatus for conducting luminescence assays, said detection module being a replaceable unit including a detection module housing, and wherein the following components are disposed within said housing:
   (a) a light detector; and
   (b) firmware configured to interface with software running on the apparatus.

2. The detection module according to claim 1, comprising an engagement mechanism for said placement and functional engagement with the apparatus.

3. The detection module according to claim 2, wherein said engagement mechanism comprises a vertical tab and the apparatus comprises an engagement pin, wherein alignment and engagement of said vertical tab and said engagement pin causes said detection module to align and engage said detection module with said apparatus.

4. The detection module according to claim 2, wherein said engagement mechanism comprises a locking mechanism configured to align with and engage said apparatus.

5. The detection module according to claim 1, further comprises an imaging system and said light detector is a component of said imaging system and said imaging system is configured to align the housing in X, Y, and/or Z-direction relative to a target positioned within said apparatus.

6. The detection module according to claim 5, wherein said target is a plate carriage, a plate carriage component, a multi-well plate, a well within a multi-well plate, a sector of said multi-well plate comprising two or more wells, and combinations thereof.

7. The detection module according to claim 5, wherein said apparatus further comprises a light-tight enclosure and said imaging system is configured to align said detection module or a component thereof with said light-tight enclosure or a component thereof.

8. The detection module according to claim 1, comprising a detection module identifier comprising detection module information selected from the group consisting of the identity of the detection module or a component thereof, the configuration of the detection module, an analytical parameter related to the use of the detection module in said apparatus, and combinations thereof.

9. The detection module according to claim 5, wherein said detection module information comprises identification information including a detection module serial number.

10. The detection module according to claim 8, wherein said detection module information comprises component identification information includes a serial number of a component of said detection module.

11. The detection module according to claim 8, wherein said apparatus further comprises a storage medium comprising detection module data and said detection module data and information is used by said apparatus to adapt and/or configure said apparatus for use with said detection module.

12. The detection module according to claim 8, wherein said detection module information comprises calibration data for use of said detection module in said apparatus.

13. The detection module according to claim 8, wherein said detection module information comprises information related to the alignment and orientation of a component of said detection module with an apparatus component.

14. The detection module of claim 8, wherein said detection module identifier is selected from the group consisting of an EEPROM, RFID, flash memory, ICC, and combinations thereof.

15. A system comprising
   (a) an apparatus for conducting luminescence assays, said apparatus comprising a light-tight enclosure (LTE), a fluidic assembly, an imaging assembly, a plate assembly capable of supporting and translating a plate to one or more components of said apparatus; and
   (b) a detection module configured for placement and functional engagement with said apparatus, said detection module is a replaceable unit disposed within a detection module housing, and wherein the following components are disposed within said housing: (x) a light detector and (y) firmware configured to interface with software running on the apparatus.

16. The system according to claim 15, the detection module comprising an engagement mechanism for said placement and functional engagement with the apparatus.

17. The system according to claim 16, wherein said engagement mechanism comprises a vertical tab and the apparatus comprises an engagement pin, wherein alignment and engagement of said vertical tab and said engagement pin causes said detection module to align and engage said detection module with said apparatus.

18. The system according to claim 16, wherein said engagement mechanism comprises a locking mechanism configured to align with and engage said apparatus.

19. The system according to claim 15, the detection module further comprising an imaging system and said light detector is a component of said imaging system and said imaging system is configured to align the housing in X, Y, and/or Z-direction relative to a target positioned within said apparatus.

20. The system according to claim 19, wherein said target is a plate carriage, a plate carriage component, a multi-well plate, a well within a multi-well plate, a sector of said multi-well plate comprising two or more wells, and combinations thereof.

21. The system according to claim 19, wherein said apparatus further comprises a light-tight enclosure and said imaging system is configured to align said detection module or a component thereof with said light-tight enclosure or a component thereof.

22. The system according to claim 15, the detection module comprising a detection module identifier comprising detection module information selected from the group consisting of the identity of the detection module or a component thereof, the configuration of the detection module, an analytical parameter related to the use of the detection module in said apparatus, and combinations thereof.

23. The system according to claim 22, wherein said detection module information comprises identification information including a detection module serial number.

24. The system according to claim 22, wherein said detection module information comprises component identification information includes a serial number of a component of said detection module.

25. The system according to claim 22, wherein said apparatus further comprises a storage medium comprising detection module data and said detection module data and information is used by said apparatus to adapt and/or configure said apparatus for use with said detection module.

26. The system according to claim 22, wherein said detection module information comprises calibration data for use of said detection module in said apparatus.

27. The system according to claim 22, wherein said detection module information comprises information related to the alignment and orientation of a component of said detection module with an apparatus component.

28. The system according to claim 22, wherein said detection module identifier is selected from the group consisting of an EEPROM, RFID, flash memory, ICC, and combinations thereof.

* * * * *